United States Patent
Zuo et al.

(10) Patent No.: US 9,970,918 B2
(45) Date of Patent: May 15, 2018

(54) PORTABLE DEVICE FOR DETECTING NUTRITION LEVEL OF PLANT

(71) Applicant: Jiangsu University, Jiangsu (CN)

(72) Inventors: Zhiyu Zuo, Jiangsu (CN); Tianyuan Lv, Jiangsu (CN)

(73) Assignee: Jiangsu University, Jiangsu (CN)

( * ) Notice: Subject to any disclaimer, the term of this patent is extended or adjusted under 35 U.S.C. 154(b) by 0 days. days.

(21) Appl. No.: 15/318,931

(22) PCT Filed: Dec. 9, 2015

(86) PCT No.: PCT/CN2015/096782
§ 371 (c)(1),
(2) Date: Dec. 14, 2016

(87) PCT Pub. No.: WO2016/201924
PCT Pub. Date: Dec. 22, 2016

(65) Prior Publication Data
US 2017/0254789 A1 Sep. 7, 2017

(30) Foreign Application Priority Data
Jun. 17, 2015 (CN) .......................... 2015 1 0334017

(51) Int. Cl.
*G01N 33/00* (2006.01)
*G01N 27/403* (2006.01)

(52) U.S. Cl.
CPC ..... *G01N 33/0098* (2013.01); *G01N 27/4035* (2013.01)

(58) Field of Classification Search
CPC ................ G01N 27/26–27/49; G01N 33/0098
See application file for complete search history.

(56) References Cited

U.S. PATENT DOCUMENTS

| 4,059,499 A | * | 11/1977 | Ibsen Nielsen | G01N 27/3335 204/418 |
| 6,398,931 B1 | * | 6/2002 | Burchette | G01N 27/333 204/416 |
| 2009/0166520 A1 | * | 7/2009 | Tuli | G01V 9/00 250/253 |
| 2015/0005964 A1 | * | 1/2015 | Liotta | A01G 7/045 700/284 |

(Continued)

FOREIGN PATENT DOCUMENTS

| CN | 1715880 A | 1/2006 |
| CN | 103278467 A | 4/2013 |

*Primary Examiner* — Huy Q Phan
*Assistant Examiner* — David Frederiksen
(74) *Attorney, Agent, or Firm* — Miller Law Group, PLLC

(57) ABSTRACT

A portable device for detecting the nutrition level of a plant includes an outer casing and a detection circuit. The outer casing includes belt pulleys, a cam, upper and lower clamping plates. The detection circuit is arranged in the outer casing and realizes an electric signal processing function and a display function. The portable device for detecting the nutrition level of the plant has the following beneficial effects: the device can be used for analyzing whether nutrient elements in crops are deficient or excessive, which is taken as the basis for accurate fertilization, and the device has low detection cost, high real-time capability, small size and is portable.

9 Claims, 2 Drawing Sheets

(56) References Cited

U.S. PATENT DOCUMENTS

| | | | | |
|---|---|---|---|---|
| 2015/0089867 A1* | 4/2015 | Abbott | .................... | A01G 9/00 47/58.1 LS |
| 2015/0323491 A1* | 11/2015 | Miller | ................ | G01N 27/4035 205/789 |

* cited by examiner

Fig. 3
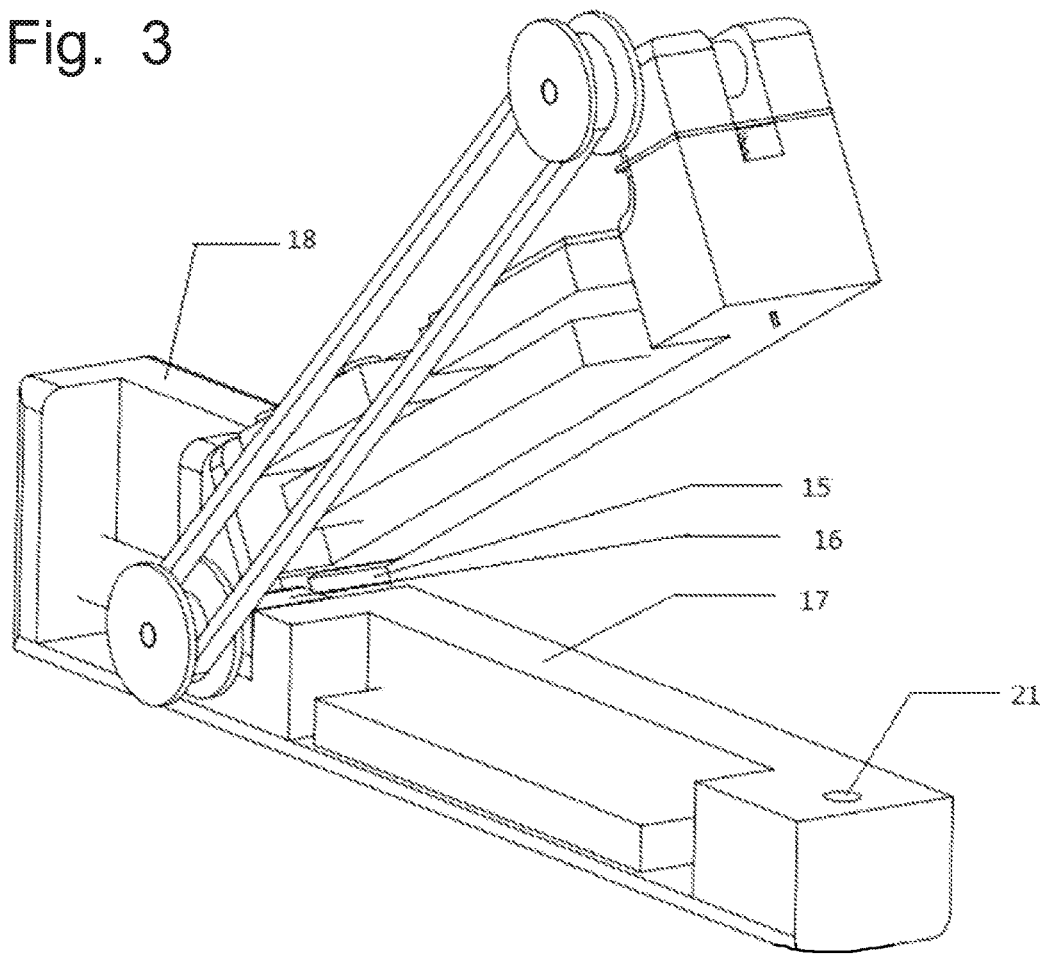
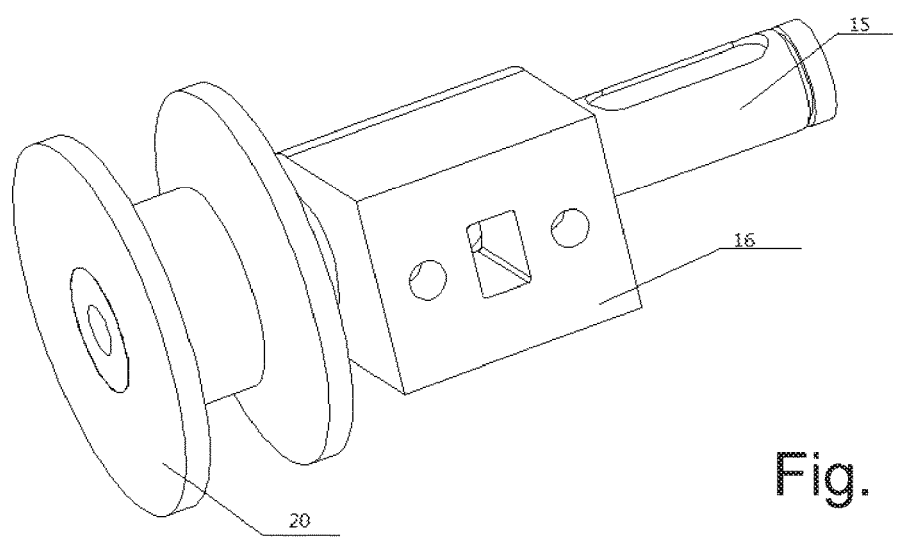
Fig. 4

PORTABLE DEVICE FOR DETECTING NUTRITION LEVEL OF PLANT

FIELD OF THE INVENTION

The present invention relates to a portable device for detecting the nutrition level of plant, in particular to a portable device for detecting the nutrition level of nitric nitrogen of plant.

BACKGROUND OF THE INVENTION

Nitric nitrogen is the necessary nutritive element for growth and metabolism in plants, and nitrogen is the component for many important organic compounds in plants, including proteins, chlorophylls, nucleic acids and a variety of bio-enzymes, therefore, both the lack and excessive application of nitric nitrogen will result in decrease of crop yield.

There are several methods for analyzing the nitric nitrogen in plants, such as a distillation process, a diffusion process and a nitrate boiling process for concentrated sulfuric acid and the like. Although the above-mentioned methods have high detection precision, they consume more time, have higher experimental cost, and have irreparable destructive effects for plants.

The ion microelectrode is capable of rapidly detecting the nutrition level of nitric nitrogen in crops. The content of nitric nitrogen can be analyzed by detecting the concentration of nitrate ions in plants. Chinese Patent No. 200510088935.0 discloses a nondestructive detection method and a portable measuring instrument for nitrogen element and moisture content in plants, which calculates the nutrition level of plants by detecting the light transmittance for fresh leaves, but has high instrument cost. Chinese Patent No. 201310164638.4 discloses a high-spectrum-based rapid nondestructive high-accuracy method for identifying the abundance degree of nitrogen element in a plant leaf, which also needs a relatively large system and cannot detect the nutrition level of the crops in real-time and on site. Sutter Company developed an ion microelectrode detection system in 2012, which is unfavorable for real-time in-vivo nondestructive detection of ion concentration in crops due to the relatively large system; furthermore, since the microelectrode is exposed to the outside, the taper end of the microelectrode is vulnerable and extremely unsafe, thus the detection cost is greatly increased.

SUMMARY OF THE INVENTION

In view of the above, the objective of the invention is to provide a portable device for detecting the nutrition level of a plant, so as to reduce the detection cost and ensure the real-time performance of detection to improve the detection accuracy.

For achieving the above objective, the present invention adopts the technical solution as follows:

A portable device for detecting nutrition level of plant, comprising an outer casing and a detection circuit, wherein:

the outer casing consists of a transmission shaft A (1), a belt pulley A (2), an electrode support (3), an upper clamping plate (19), a concave platform (4), a belt (5), a belt pulley B (10), a cam (12), a spring (13), a rotating shaft A (15), a rotating shaft B (16), a lower clamping plate (17), a battery housing (18) and a transmission shaft B (20);

one end of the transmission shaft A (1) is supported at a center position in a rear plane of the concave platform (4) on the right side of the upper clamping plate (19), while the other end of the transmission shaft A (1) is connected with the belt pulley A (2); the transmission shaft A (1) passes through the cam (12); the cam (12) is fixed to a middle part of the transmission shaft A (1); the belt pulley A (2) drives the cam (12) to rotate through the transmission shaft A (1), thereby causing the electrode support (3) to move up and down; one end of the spring (13) is fixed to a concave surface in the middle of the concave platform (4), while the other end is fixed to a center position of the electrode support (3); a measuring electrode (14) passes through the spring (13) and is fixed to the center position of the electrode support (3);

the belt pulley A (2) is connected with the belt pulley B (10) through the belt (5); the belt pulley B (10) is fixedly connected with the rotating shaft B (16); the rotating shaft B (16) is fixed to the left side of the lower clamping plate (17), a circular section of the rotating shaft B (16) coincides with a front surface of the lower clamping plate (17); the other end of the circular section of the rotating shaft B (16) is in nested connection with the rotating shaft A (15); the other end of the rotating shaft A (15) is fixed to the left side of the upper clamping plate (19); when the upper clamping plate (19) rotates, the transmission shaft B (20) is driven to rotate by the rotating shaft A (15), thereby driving the belt pulley B (10) to rotate; the belt pulley B (10) drives the belt pulley A (2) to rotate through the belt (5);

the detection circuit consists of a display screen (6), a matrix keyboard (8), a signal processing circuit (7), a battery (9), a power module (11) and a measuring electrode (14);

in the detection circuit, an input end of the signal processing circuit (7) is in parallel connection with a nitrate ion signal line and a reference signal line extending from the measuring electrode (14); an output end of the signal processing circuit (7) is connected with an input end of the display screen (6); the matrix keyboard (8) is connected with the input end of the signal processing circuit (7); a filter circuit, an analog-to-digital converter and a single-chip processing circuit are integrated in the signal processing circuit (7); the battery (9) consists of two pieces of AA batteries of 1.5V; an operating voltage is supplied for the keyboard (8), the display screen (6) and the signal processing circuit (7) by the power module (11).

The outer casing further comprises a protective hole (21), which is located at 3 cm away from a right boundary of the lower clamping plate (17), and internally filled with sponges; when the measuring electrode (14) extends out of the upper clamping plate (19), a taper end of the measuring electrode (14) directly faces the center of the protective hole (21). The invention has the following advantages due to the use of the above technical solution:

1. in the present invention, with an integrated circuit design, and as a parallel structure of a double-barreled glass microelectrode of the measuring electrode only can detect one type of ion concentration per time, the complexity of the circuit is greatly reduced so as to reduce the volume and cost of the portable device for detecting the nutrition level of a plant; the in-vivo nondestructive measurement can be performed on crop leaves in real-time to obtain the nitrate ion concentration, so as to improve the detection accuracy.

2. in the present invention, the measuring electrode can move up and down by the belt pulley A, the belt pulley B, the belt, the cam and the spring structure; the measuring electrode extends out of the upper clamping plate only when detecting the crop leaves and retracts back into the upper clamping plate when the detection is finished; the probability for damage to the measuring electrode is greatly reduced, thus the detection cost is reduced and the safety is increased.

BRIEF DESCRIPTION OF THE DRAWINGS

FIG. 3 is an overall structural diagram of the present invention.
FIG. 4 is a structural diagram of the driven transmission shaft nested with a rotating shaft fixed to the upper clamping plate.

DETAILED DESCRIPTION OF THE PREFERRED EMBODIMENT

The invention is described in detail below in conjunction with the accompanying drawings and examples.

The present invention provides a portable device for detecting nutrition level of plant, comprising a measuring electrode 14 with a parallel double-barreled glass microelectrode structure. The lower ends of each glass microelectrodes in the measuring electrode 14 are pulled into a taper shape and are tightly arranged in parallel for fixation. The regular silanization treatment is performed on the inner walls of two micro glass pipes, and the microelectrodes are continuously baked in an oven at 150 degrees for 60-120 minutes. Firstly, a nitrate ion sensitizer with a liquid column length of 0.5 mm is filled in a taper end of the first micro glass pipe, and a nitrate ion inner filling liquid with a liquid column length of 25 mm is filled subsequently; then, one end of the nitrate ion signal line is inserted into the nitrate ion inner filling liquid, while the other end extends out of the micro glass pipe and is fixed with a sealing glue at the pipe opening. A reference signal inner filling liquid with a liquid column length of 30 mm is filled in a taper end of another micro glass pipe; one end of the reference signal line is inserted into the reference inner filling liquid, while the other end extends out of the micro glass pipe and is fixed with the sealing glue at the pipe opening.

In which, the nitrate ion sensitizer is Ammonium ionophore I cocktail A of Sigma-Aldrich Company, the ammonium ion sensitizer is Nitrate ionophore cocktail A of Sigma-Aldrich Company. Three micro glass pipes are single-pipe micro glass pipes of Hilgenberg Company; the nitrate ion inner filling liquid is a mixed solution of 50 mM $KNO_3$; the reference inner filling liquid is 200 mM KCl solution; the ammonium ion inner filling liquid is 50 mM KCl solution; all of the nitrate ion signal line, the reference signal line and the ammonium ion signal line use an AgCl thread made from silver wires with a purity of 99% and a diameter of 0.3 mm by a regular electroplating method.

Figure 1:
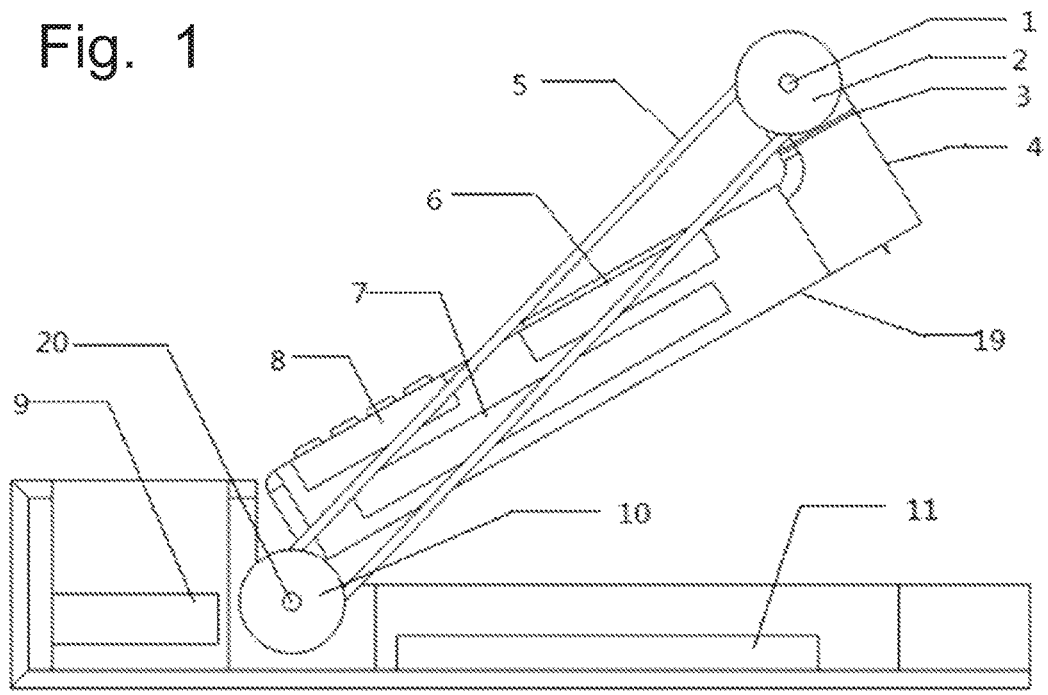
FIG. 1 is a front view of the present invention.
Figure 2:
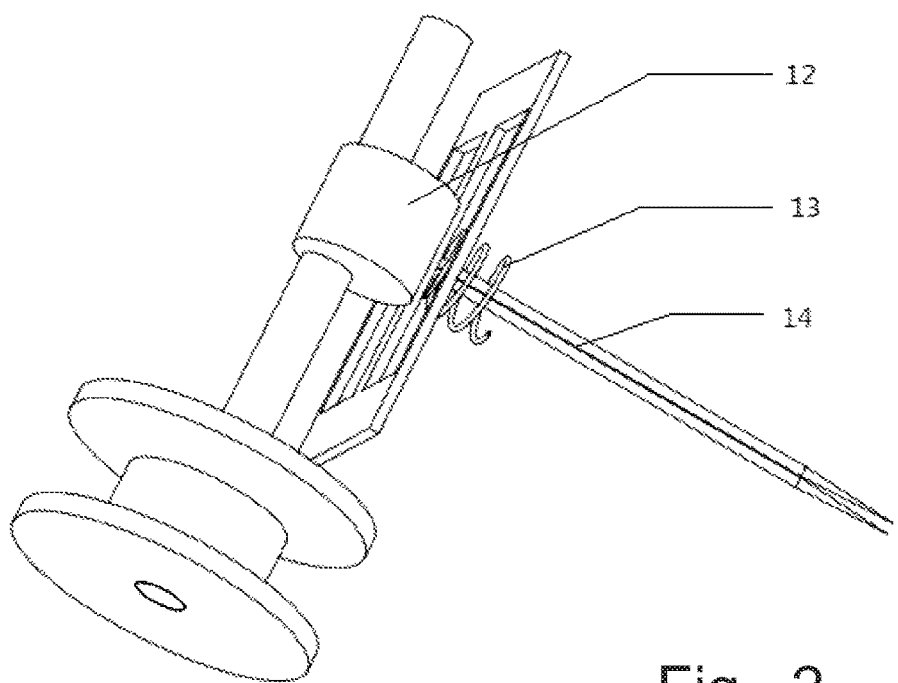
FIG. 2 is a structural diagram of the measuring electrode and the cam portion of the present invention.

As shown in FIGS. 1, 2 and 3, the outer casing consists of a transmission shaft A 1, a belt pulley A 2, an electrode support 3, an upper clamping plate 19, a concave platform 4, a belt 5, a belt pulley B 10, a cam 12, a spring 13, a rotating shaft A 15, a rotating shaft B 16, a lower clamping plate 17, a battery housing 18, a transmission shaft B 20 and a protective hole 21; the detection circuit consists of a display screen 6, a matrix keyboard 8, a signal processing circuit 7, a battery 9, a power module 11, and a measuring electrode 14.

One end of the transmission shaft A 1 is supported at a center position in a rear plane of the concave platform 4 on the right side of the upper clamping plate 19, while the other end of the transmission shaft A 1 is connected with the belt pulley A 2; moreover, the cam 12 is fixed together with the transmission shaft A 1 that passes through the cam 12. One end of the spring 13 is fixed to a concave surface in the middle of the concave platform 4, while the other end is fixed to the center position of the electrode support 3; the measuring electrode 14 passes through the spring 13 and is fixed to the center position of the electrode support 3; the belt pulley A 2 is connected with the belt pulley B 10 through the belt 5; the belt pulley B 10 is fixedly connected with the rotating shaft B 16 that is fixed to the left side of the lower clamping plate 17; a circular section of the rotating shaft B 16 coincides with a front surface of the lower clamping plate 17. As depicted in FIG. 4, the other end of the circular section of the rotating shaft B 16 is in nested connection with the rotating shaft A 15, the other end of the rotating shaft A 15 is fixed to the left side of the upper clamping plate 19; when the upper clamping plate 19 rotates, the transmission shaft B 20 is driven to rotate by the rotating shaft A 15, thereby driving the belt pulley B 10 to rotate; the belt pulley B 10 drives the belt pulley A 2 to rotate through the belt 5; in the detection circuit, a nitrate ion signal line and a reference signal line extending out of the measuring electrode 14 are connected in parallel to an input end of the signal processing circuit 7; an output end of the signal processing circuit 7 is connected with an input end of the display screen 6; the matrix keyboard 8 is connected with the input end of the signal processing circuit 7; a filter circuit, an analog-to-digital converter and a single-chip processing circuit are integrated in the signal processing circuit 7; the battery 9 consists of two pieces of AA batteries of 1.5V; an operating voltage is supplied for the keyboard 8, the display screen 6 and the signal processing circuit 7 by the power module 11.

During detection, a part to be detected of the leaf is laid right above the protective hole 21 and the upper clamping plate 19 is slowly closed; at this point, the rotating shaft A 15 drives the transmission shaft B 20 to rotate, thereby driving the belt pulley B 10 to rotate clockwise; the belt pulley B 10 drives the belt pulley A 2 to rotate clockwise through the belt 5; the belt pulley A 2 rotates so as to drive the cam 12 to rotate through the transmission shaft A 1; the cam 12 rotates to press the electrode support 3, causing the electrode support 3 to move down perpendicular to the upper clamping plate 19; the measuring electrode 14 extends out of the upper clamping plate 19 to penetrate into the part to be detected of the leaf.

At this point, since the nitrate ion can be adhered to the nitrate ion signal line through the nitrate ion sensitizer due to the action of the nitrate ion sensitizer and there is no nitrate ion in the reference signal line, a potential difference is generated between the nitrate ion signal line and the reference signal line. The potential difference signal is transferred to the input end of the signal processing circuit 7 for processing to obtain the concentration of the nitrate ion and thereby obtain the concentration of nitric nitrogen. The concentration is sent to the display screen 6 for display.

After the detection is completed, the upper clamping plate 19 is raised, the rotating shaft A 15 drives the transmission shaft B 20 to rotate, thereby driving the belt pulley B 10 to rotate anticlockwise; the belt pulley B 10 drives the belt pulley A 2 to rotate, thereby driving the cam 12 to rotate; the electrode support 3 is raised under the counter-acting force of the spring 13; the measuring electrode 14 retracts back into the upper clamping plate 19.

The invention claimed is:
1. A portable device for detecting the nutrition level of a plant, comprising:

an outer casing including a transmission drive shaft coupled to a transmission driven shaft by a power transmission assembly, said transmission driven shaft being connected to a cam, an electrode support being biased into engagement with said cam by a spring, said transmission drive shaft being connected to a first rotating shaft and to a second rotating shaft, one end of the transmission driven shaft being supported at a center position in a rear plane of a concave platform on a side of an upper clamping plate, while an opposing end of the transmission driven shaft is connected with the power transmission assembly, the transmission driven shaft passes through the cam which is located at an intermediate part of the transmission driven shaft, the rotation of the transmission driven shaft rotates the cam thereby causing the electrode support to move up and down in response to engagement with the rotating cam, the second rotating shaft is fixedly connected to the power transmission assembly and is fixed to a selected side of a lower clamping plate, one end of the second rotating shaft is in a nested connection with the first rotating shaft, while an opposing end of the first rotating shaft is fixed to the selected side of the upper clamping plate such that when the upper clamping plate rotates, the transmission drive shaft is rotated by the first rotating shaft thereby driving the rotation of the power transmission assembly; and a detection circuit having a display screen, a matrix keyboard, a signal processing circuit, a power source, a power module and a measuring electrode fixed to a central position of the electrode support, an input end of the signal processing circuit is in parallel connection with a nitrate ion signal line and a reference signal line extending from the measuring electrode, an output end of the signal processing circuit is connected with an input end of the display screen.

2. The portable device for detecting the nutrition level of a plant according to claim 1 wherein the outer casing further comprises a protective hole in the lower clamping plate and being filled internally with sponges, the measuring electrode being positioned to extend out of the upper clamping plate when moved by said cam such that a tapered end of the measuring electrode directly faces the center of the protective hole.

3. The portable device for detecting the nutrition level of a plant according to claim 1 wherein the power transmission assembly includes a first belt pulley connected to said transmission driven shaft, a second belt pulley connected to said transmission drive shaft with a belt entrained around said first and second belt pulleys to transfer rotation between said transmission drive shaft and said transmission driven shaft.

4. The portable device for detecting the nutrition level of a plant according to claim 1 wherein the one end of the spring is fixed to a concave platform, while the other end of the spring is fixed to a center position of the electrode support.

5. The portable device for detecting the nutrition level of a plant according to claim 1 wherein a circular section of the second rotating shaft coincides with a front surface of the lower clamping plate.

6. The portable device for detecting the nutrition level of a plant according to claim 1 wherein the matrix keyboard is connected with the input end of the signal processing circuit, said detection circuit further including a filter circuit, an analog-to-digital converter and a single-chip processing circuit integrated in the signal processing circuit.

7. The portable device for detecting the nutrition level of a plant according to claim 6 wherein the power source is a battery comprises two AA batteries of 1.5V each, providing an operating voltage for operation of the keyboard, the display screen and the signal processing circuit by the power module.

8. A portable device for detecting the nutrition level of a plant, comprising:
   an outer casing and a detection circuit, wherein:
   the outer casing consists of a transmission shaft A, a belt pulley A, an electrode support, an upper clamping plate, a concave platform, a belt, a belt pulley B, a cam, a spring, a rotating shaft A, a rotating shaft B, a lower clamping plate, a battery housing and a transmission shaft B;
   one end of the transmission shaft A is supported at a center position in a rear plane of the concave platform on the right side of the upper clamping plate, while the other end of the transmission shaft A is connected with the belt pulley A, the transmission shaft A passes through the cam, the cam is fixed to a middle part of the transmission shaft A, the belt pulley A drives the cam to rotate through the transmission shaft A, thereby causing the electrode support to move up and down, one end of the spring is fixed to a concave surface in the middle of the concave platform, while the other end of the spring is fixed to a center position of the electrode support, a measuring electrode passes through the spring and is fixed to the center position of the electrode support;
   the belt pulley A is connected with the belt pulley B through the belt, the belt pulley B is fixedly connected with the rotating shaft B, the rotating shaft B is fixed to the left side of the lower clamping plate, a circular section of the rotating shaft B coincides with a front surface of the lower clamping plate, the other end of the circular section of the rotating shaft B is in nested connection with the rotating shaft A, the other end of the rotating shaft A is fixed to the left side of the upper clamping plate, when the upper clamping plate rotates, the transmission shaft B is driven to rotate by the rotating shaft A, thereby driving the belt pulley B to rotate, the belt pulley B drives the belt pulley A to rotate through the belt;
   the detection circuit consists of a display screen, a matrix keyboard, a signal processing circuit, a battery, a power module and a measuring electrode;
   in the detection circuit, an input end of the signal processing circuit is in parallel connection with a nitrate ion signal line and a reference signal line extending from the measuring electrode; an output end of the signal processing circuit is connected with an input end of the display screen; the matrix keyboard is connected with the input end of the signal processing circuit, a filter circuit, an analog-to-digital converter and a single-chip processing circuit are integrated in the signal processing circuit, the battery consists of two pieces of AA batteries of 1.5V each to provide an operating voltage for the keyboard, the display screen and the signal processing circuit by the power module.

9. The portable device for detecting the nutrition level of a plant according to claim 8, wherein the outer casing further comprises a protective hole, which is located at 3 cm away from a right boundary of the lower clamping plate, and internally filled with sponges, when the measuring electrode extends out of the upper clamping plate, a tapered end of the measuring electrode directly faces the center of the protective hole.

\* \* \* \* \*